United States Patent [19]

Saxena

[11] Patent Number: 4,840,730

[45] Date of Patent: * Jun. 20, 1989

[54] CHROMATOGRAPHY SYSTEM USING HORIZONTAL FLOW COLUMNS

[75] Inventor: Vinit Saxena, Pinole, Calif.

[73] Assignee: Sepragen Corporation, San Leandro, Calif.

[ * ] Notice: The portion of the term of this patent subsequent to Dec. 9, 2003 has been disclaimed.

[21] Appl. No.: 207,896

[22] Filed: Jun. 9, 1988

Related U.S. Application Data

[63] Continuation of Ser. No. 889,335, Jul. 25, 1986, abandoned.

[51] Int. Cl.$^4$ ............................................... B01D 15/08
[52] U.S. Cl. ................................. 210/198.2; 210/96.1; 210/103; 210/137; 210/143; 210/232; 210/282; 210/659
[58] Field of Search ...................... 210/96.1, 103, 137, 210/143, 232, 238, 282, 659; 422/70

[56] References Cited

U.S. PATENT DOCUMENTS

| | | | |
|---|---|---|---|
| 2,370,190 | 2/1945 | Ralston | 210/282 |
| 2,708,519 | 5/1955 | Novak | 210/198.2 |
| 3,529,726 | 9/1970 | Keenan | 210/282 |
| 3,686,117 | 8/1972 | Lauer | 210/659 |
| 3,701,609 | 10/1972 | Bailey | 210/198.2 |
| 3,786,920 | 1/1974 | Raymond | 210/232 |
| 3,862,038 | 1/1975 | Takeuchi | 210/198.2 |
| 4,116,046 | 9/1978 | Stein | 210/198.2 |
| 4,128,476 | 12/1978 | Rock | 210/659 |
| 4,154,583 | 5/1979 | Favre | 210/198.2 |
| 4,271,697 | 6/1981 | Mowery | 210/198.2 |
| 4,311,586 | 1/1982 | Baldwin | 210/198.2 |
| 4,347,131 | 8/1982 | Brownlee | 210/198.2 |
| 4,357,668 | 11/1982 | Schwartz | 210/198.2 |
| 4,379,751 | 4/1983 | Yoritomi | 210/659 |
| 4,416,775 | 11/1983 | Halbich | 210/282 |
| 4,422,942 | 12/1983 | Allington | 210/659 |
| 4,476,017 | 10/1984 | Scharff | 210/94 |
| 4,496,461 | 1/1985 | Leeke | 210/198.2 |
| 4,595,495 | 6/1986 | Yotam | 210/198.2 |
| 4,627,918 | 12/1986 | Saxena | 210/198.2 |
| 4,676,898 | 6/1987 | Saxena | 210/198.2 |

OTHER PUBLICATIONS

Snyder, Introduction to Modern Liquid Chromatography John Wiley & Sons, Inc. New York, 1979, pp. 519-520.

Primary Examiner—Ernest G. Therkorn
Attorney, Agent, or Firm—Shyamala T. Rajender

[57] ABSTRACT

A system for chromatography using horizontal (radial) flow columns is disclosed. The system provides rapid separation of complex biological or organic mixtures at low operating pressures. The system may be used in a variety of applications, such as in the analysis of the constituents of a mixture, or in large pilot or plant scale operations where the isolation of one or more purified components of a mixture or fluid is required for further testing or for commercial purposes. The system is designed to accommodate separation via a variety of routes including ion-exchange, affinity, hydrophobic, chiral, hydroxylapatite, reverse phased as well as rapid desalting techniques.

22 Claims, 4 Drawing Sheets

CHROMATOGRAPHY SYSTEM USING HORIZONTAL FLOW COLUMNS

This is a continuation of application Ser. No. 889,335 filed on July 25, 1986, now abandoned.

This invention relates to an integrated system for performing rapid and high performance chromatography at low operating pressures; particularly to a system capable of small size operations such as analytical applications and larger size operations, such as those used for pilot or production applications; and more particularly to such a system using horizontal flow in both isocratic and gradient operations.

BACKGROUND OF THE INVENTION

Both isocratic and gradient chromatography systems are known in the prior art, each being utilized for specific applications and each utilizing the same basic components.

A complete, turnkey isocratic chromatographic system consists of the following components:

1. A chromatography column containing column packings or separation medium wherein the actual separation takes place.
2. A pump, syringe, sample injector or a sample loop to inject a sample onto the column.
3. A fluid delivery system, such as a metering pump, to feed starting, elution or wash buffer materials into the column.
4. A detector (which measures for example, absorption or emission in the ultraviolet, infrared, visible region, electrochemical potential, radioactivity, conductivity etc.,) to measure the concentration of the components in the separated stream coming out of the column.
5. A fraction collector which collects various fractions of components separated on the column and eluted at different rates. The fraction collector can be programmed to do the collection as a function of time, volume, number of drops per unit time or peak collection based on input from the detector.
6. Various other monitors, e.g., pressure and flow, to establish the status of the process at any given time.
7. Data acquisition equipment which records the chromatograms of the eluting compounds and can calculate the composition of the various components.
8. A process controller, which may be in the form of a computer or microprocessor, to interface with each of the above-described components.
9. Assorted piping and valving.

A gradient chromatography system uses the same general components as the isocratic system, the primary difference being in the solvent delivery which has to deliver a mixture of fluids whose composition varies continuously as a function of time. The gradient technique is often used to separate peaks that may elute close together in an isocratic mode and need small changes in elution conditions to achieve differential separation. This is accomplished by using two pumps, each of which is connected to a particular buffer chamber, and independently pump the fluid streams into a mixer where both the buffers are mixed and the mixture is them delivered to the column. The pumping rates are controlled by a gradient programmer which is designed to vary the flow rates to achieve the desired combination of flow rate and composition.

In many instances where the limit buffer is responsible for creating a specific gradient (e.g., ionic or pH) an additional detector, such as a pH meter or conductivity meter, may be used downstream of the column to monitor the gradient profile.

In the last decade, many advancements have been made, as integrated chromatographic systems have become more sophisticated and responsive. For example, the need for faster separations with higher resolution have given rise to rigid, small size column packings as opposed to larger size soft gels. The newer, high performance liquid chromatography (HPLC) systems, however, operate at very high pressures, such as 1000–4000 psi, which requires special pumps, high pressure tubing and valving, and special column and accessory designs. The cost of these systems, consequently, is very high.

As the need for higher performance has started to extend beyond the analytical laboratory to production chromatography systems, the problem has taken on a new dimension. The cost of preparative systems has escalated tremendously. Furthermore, such systems operating at these high pressures are being used in routine production environment, which can be a serious hazard. The industry is thus in the position of having to choose between low pressure, low cost systems which are slow and have limited purification capabilities, or high pressure, high performance systems which are significantly more expensive and pose a health hazard. Thus, a need exists in the art of chromatography for a system which is capable of high performance without resorting to high pressure and the associated hazards and high costs.

Therefore, it is an object of this invention to provide a chromatography system capable of high performance while operating at relatively low pressures.

Another object of this invention is to provide a chromatography system, either isocratic, gradient or ternary, which utilizes horizontal flow through the separation medium in the columns, while providing low pressure, high performance operation.

A further object of this invention is to provide a chromatography system using horizontal (radial) flow columns capable of use in analytical, pilot or production applications.

Another object of the invention is to provide a chromatography system capable of use in both isocratic and gradient applications and which produces rapid separations with either conventional gels or with high performance packings, without high operating pressures and high equipment cost.

Additional objects, advantages and novel features of the invention, together with additional features contributing thereto and advantages accruing therefrom will be apparent to those skilled in the art, from the following description of the invention which is shown in the accompanying drawings which are incorporated herein by reference and form an integral part hereof. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention as broadly described herein, the subject invention is directed to a chromatography system which utilizes horizontal flow columns and low operating pressures. The system of this invention may be of either the isocratic, gradient, or ternary type and is capable of giving rapid separations either with conventional gels or with high performance packings without high operating pressure and high equipment costs.

The horizontal (radial) flow columns utilized in the system of this invention may be, for example, of the type described and claimed in application Ser. No. 794,727 filed Nov. 4, 1985 and entitled "Chromatography Column Using Horizontal Flow", now U.S. Pat. No. 4,627,918 issued Dec. 9, 1986, and/or application Ser. No. 06/869,295, filed June 2, 1986, entitled "Improved Chromatography Column Using Horizontal Flow", now U.S. Pat. No. 4,676,898, issued June 30, 1987 which disclosures are incorporated herein by reference thereto. The horizontal (radial) flow column gives high cross-sectional areas and low bed height. This results in a low pressure drop across the column even at high flow rates.

The implications of the low pressure is that low pressure solvent delivery pumps, low pressure tubing and valves, and accessories and column components can be used in the system, thus reducing the cost of such components of the system. Now, separation based on both conventional soft gels and high performance media can be done on this system. Thus, this allows the user tremendous flexibility and reduction in cost. The system provides for separation via a variety of routes including but not limited to absorption-desorption, ion exchange, affinity, hydrophobic, hydrophilic, chiral, hydroxylapatite, reverse phase and rapid desalting techniques.

By utilizing horizontal flow chromatography columns in the system of this invention, the system can be scaled down to be used in the analysis of constituents as well as made larger for pilot or plant systems. In addition, the horizontal flow chromatography columns made in accordance with the inventions of the above-referenced applications, enable scaling down even to semipreparative levels by the use of a disposable horizontal (or radial) flow column, as well as providing for stacking of the columns, i.e., the use of a smaller column as a precolumn or a guard column or the uses of the second column as a post column reactor.

The system of this invention may incorporate a stand to accommodate the smaller size columns. The stand functions as a sturdy holder for the column(s) and is designed such that the end user raise or lower the column and have access to the column fittings. It also serves to prevent the column from breakage by toppling or falling over.

The system of this invention, which utilizes horizontal (radial) flow columns, is constructed and arranged to do rapid separations of complex biological or organic mixtures at low operating pressure, regardless of the media of which the separation bed is composed (conventional gels or high performance packings).

DETAILED DESCRIPTION OF THE INVENTION

The invention is directed to chromatographic systems using horizontal (radial) flow separation columns. The chromatography columns may be of the type described and claimed in the two copending patent applications referred to above. The system is designed to do rapid separations of complex biological or organic mixtures at low operating pressures, and may be used with columns containing conventional gels or high performance packings, thus eliminating problems associated with high operating pressures and the resulting hazards and high costs. The separation columns used in the systems of this invention, which utilize horizontal (radial) flow through the separation medium, as opposed to vertical, axial or spiral flow, the columns give high cross-sectional areas and low bed height. This results in a low pressure drop across the column even at high flow rates. As used herein, the terms "horizontal flow" or "radial flow" is defined as any fluid flow through the column in a direction that is substantially perpendicular to the longitudinal axis of the column measured in terms of the distance between the top and bottom plates, regardless of the position of the column, whether it is used in a vertical, horizontal or slanted position, depending upon the setting and application.

The system of this invention may have various applications. For example, it may be used in the analysis of the constituents of a mixture or it may be used in larger pilot, production or plant scale operation where the isolation of one or more purified components is required for further testing or for commercial production. The systems are designed to accommodate separations via a variety of routes including but not limited to ion-exchange, affinity, hydrophobic, hydrophilic, hydroxylapatite, reverse phase, chiral and rapid desalting techniques. By utilizing horizontal flow chromatographic columns such as those described in the latter of the two above identified copending patent applications, which utilize disposable separation packing material and which are scaled down to small size for semi-preparative levels, the system of this invention provides the user with a great deal of flexibility.

Included, for use in the system of this invention, is an embodiment of a stand designed to accommodate the horizontal flow columns, particularly those small columns involved with analytical and semi-preparative analyses, which incorporate air discharge means to eliminate void volume within the columns as well as providing for stacking of the smaller size columns to increase their capacity. While only one column is illustrated in the stand, it is constructed to enable two or more columns to be stacked, one above the other, depending on the height of the columns.

While the embodiments of the systems illustrated and described herein are directed to gradient chromatography, with minor modifications in the solvent delivery arrangements, as known in the art, the systems may be utilized for either isocratic or ternary chromatography applications, while still maintaining the low pressure operation and the associated lower costs of production and operation. For example, the system of this invention operates at pressures of less than 100 psi, whereas prior known systems operate at pressures in the range of about 2000–4000 psi in high performance liquid chromatography (HPLC) applications. Thus, the reduction in the cost of these systems stems from the use of pumps, valves, tubing, detectors etc., which do not need high pressure capabilities. With the systems of the present invention, the end user is no longer required to choose between low pressure, low cost systems which are slow and have limited purification capabilities or high pressure, high performance systems which are significantly more expensive.

Figure 1:
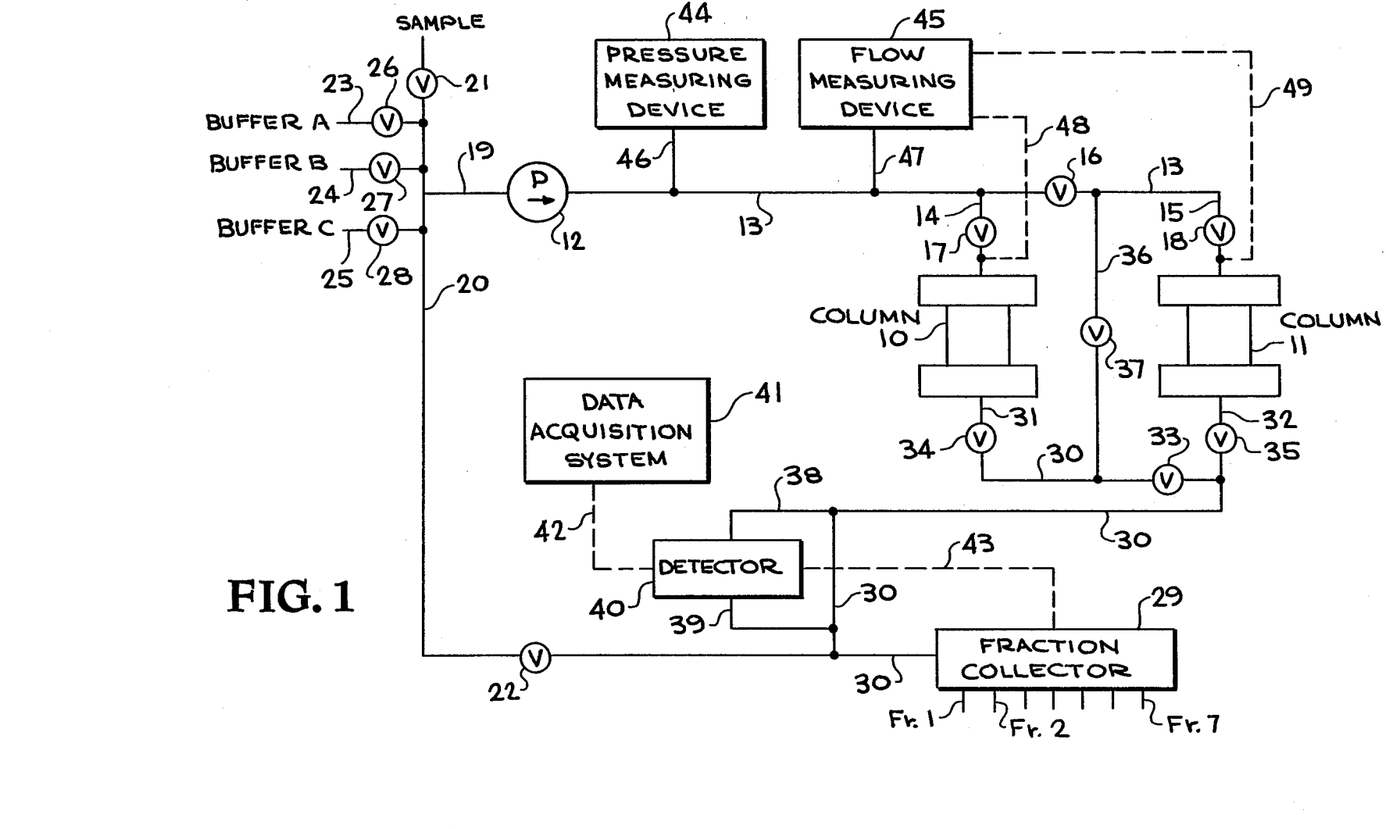
FIG. 1 schematically illustrates an embodiment of the invention for single or multiple gradient elution chromatography.
Figure 2:
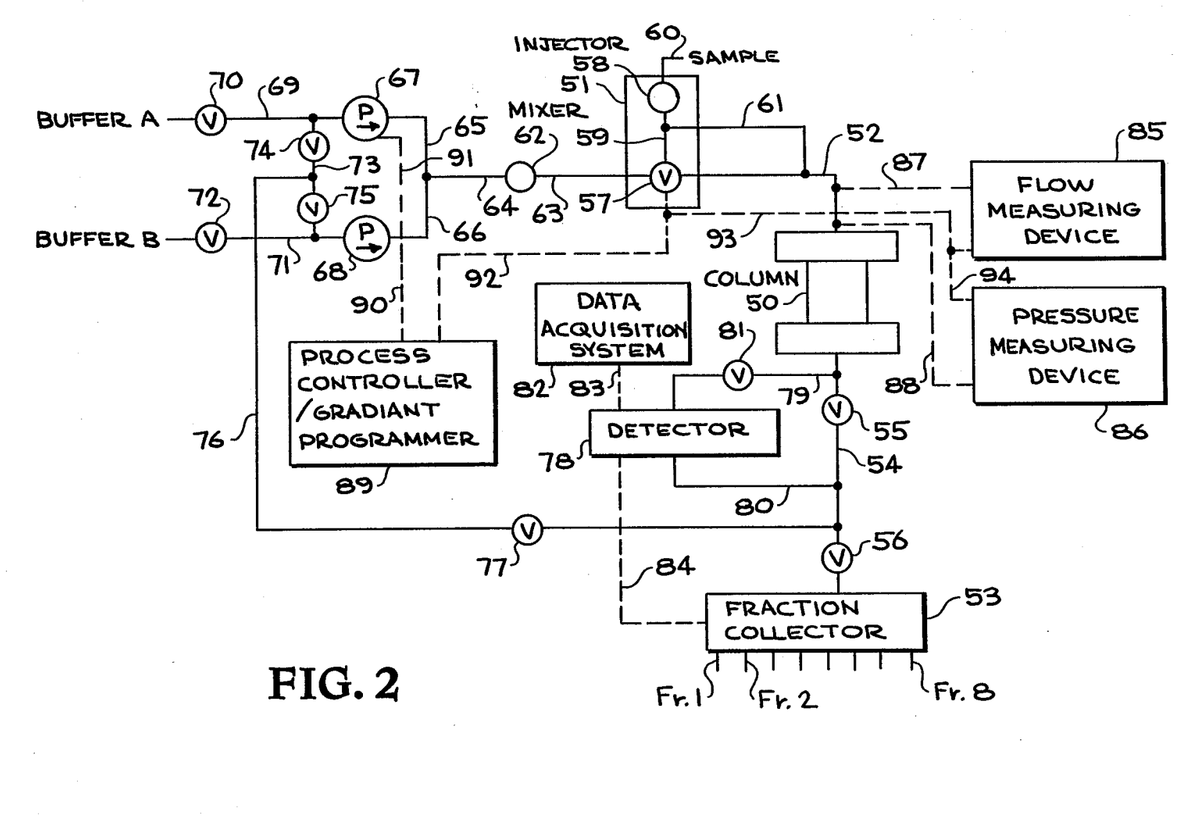
FIG. 2 schematically illustrates an embodiment of the invention for continuous gradient chromatography.
Figure 3:
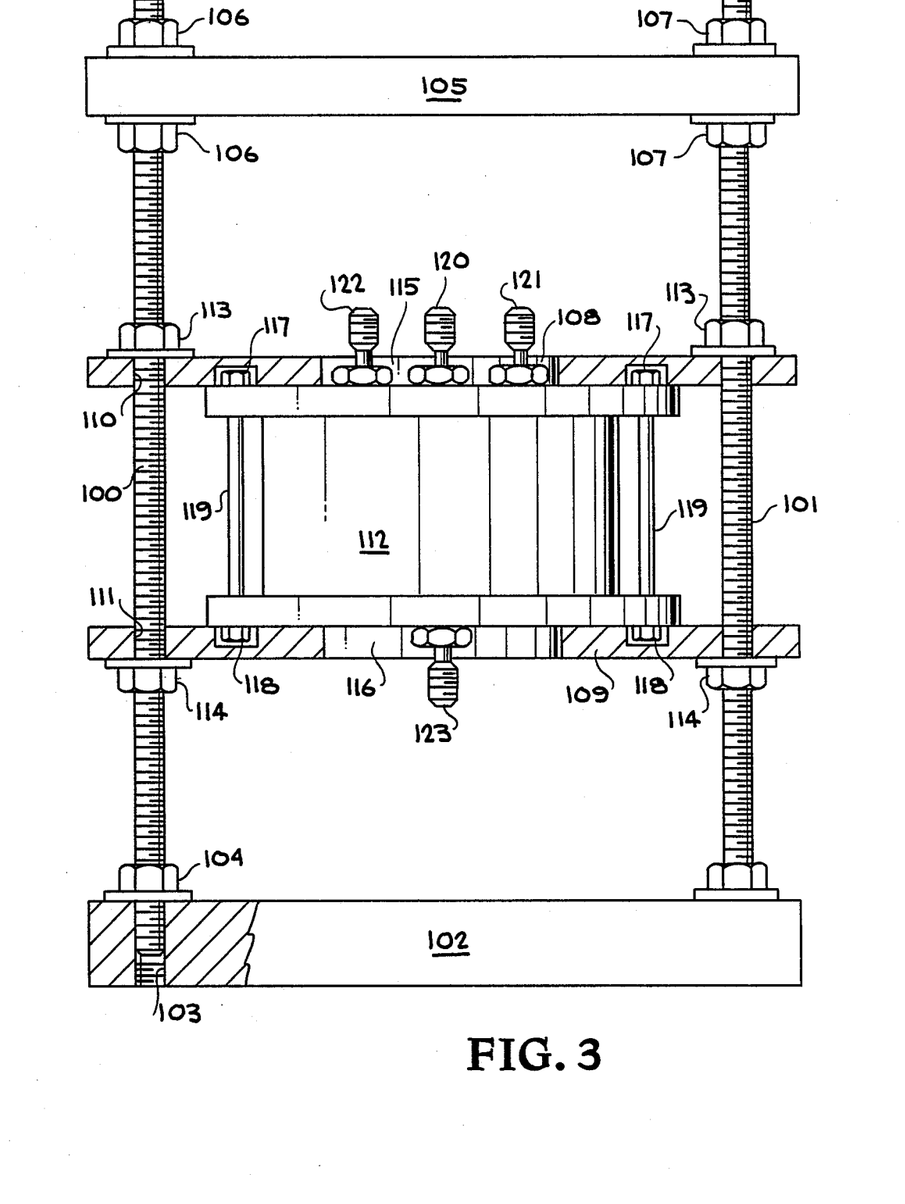
FIG. 3 is an embodiment of a support stand for the chromatographic columns of the systems depicted in FIGS. 1 and 2.

Referring now to the drawings, FIG. 1 illustrates an embodiment of the invention for using single or multiple gradient elution chromatography, with FIG. 2 illustrating an embodiment for continuous gradient chromatography. FIG. 3 illustrates an embodiment of a column stand for stacking or ready relocation or movement of the columns used in the systems of FIGS. 1 and 2.

Figure 4:
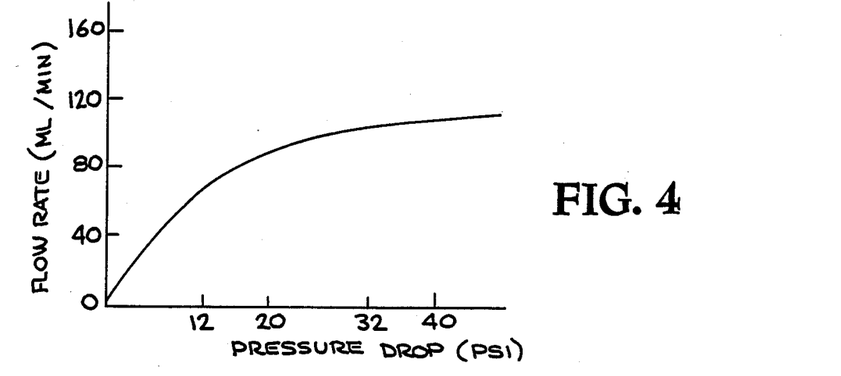
FIG. 4 is a graph showing pressure drop across the column as a function of flow rate.
Figure 5:
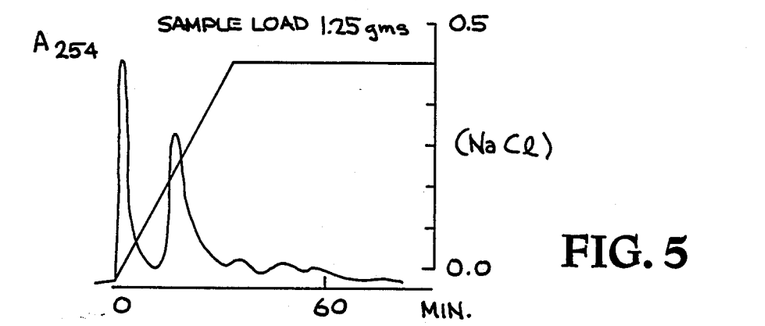
FIG. 5 is a graph showing the fractionation of bovine serum albumin with the column of this invention using DEAE-cellulose as the separation medium.
Figure 6:
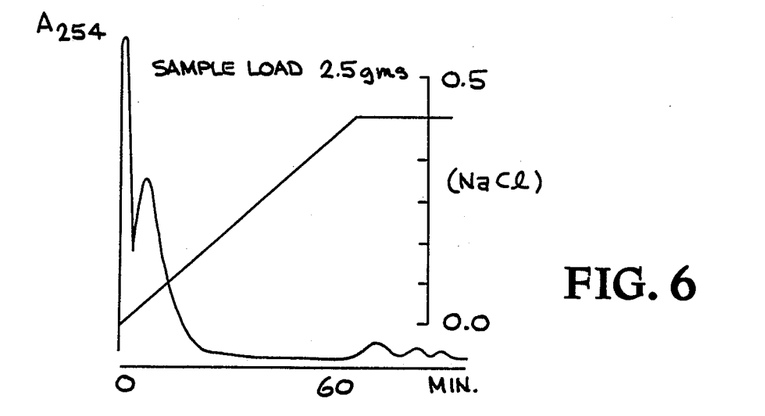
FIG. 6 is a graph showing a scale up of the fractionation of FIG. 5.

FIGS. 4, 5, and 6 illustrate, respectively, the pressure drop across the column as a function of the flow rate, the fractionation of bovine serum albumin with the instant column, using DEAE cellulose as the separation medium and a scale up of the same fractionation, using a larger sample size.

The chromatography system using horizontal (radial) flow columns illustrated in FIG. 1 basically comprises a plurality, only a pair shown, of separation columns, a metering pump connected between a plurality of buffer supplies and the columns, pressure and flow measuring devices, a detector, a data acquisition system, and a fraction collector, interconnected by tubing or piping valves, and feedback or control lines or signals. The columns may be connected in series or parallel, depending on whether a greater resolution or greater throughput is desired. The columns may be of the construction illustrated in the earlier identified copending patent applications, the disclosures of which are incorporated herein by reference thereto. In the embodiment of FIG. 1, the separation columns may be used in series or in parallel. As shown, the system includes a pair of horizontal (radial) flow columns 10 and 11 each connected at the inlets thereof to an outlet of a metering pump 12 via a fluid line (tubing, conduit or pipe) indicated at 13 and branch lines 14 and 15, with a valve 16 located in line 13 and valves 17 and 18 located in branches 14 and 15, respectively. Metering pump 12 is connected at the inlet thereof via a fluid line (pipe, tubing or conduit) 19 to a sample supply line 20 having therein a pair of spaced valves 21 and 22, line 20 being connected to three (3) lines 23, 24 and 25, having valves 26, 27 and 28 respectively and which are connected to sources identified as buffer material A, buffer material B and buffer material C. The outlets of each of columns 10 and 11 are connected to a detector 40, either directly or via a stream splitter and a fraction collector 29 via a fluid line (pipe, tubing or conduit) 30 and branch lines 31 and 32, with a valve 33 located in line 30 and valves 34 and 35 located in branches 31 and 32 respectively. Lines 13 and 30 are interconnected by a line 36 having therein a valve 37. Thus, the columns 10 and 11 may be connected to metering pump 12 and fraction collector 29 in either a series or parallel relation. For series operation of the columns 10 and 11, valve 16 is closed, valve 17 is open, valve 34 is open, valve 33 is closed and valves 37, 18 and 35 are open, thereby establishing sequential flow through lines 13, 14, column 10, lines 31, 30, 36, 13, 15, column 11, lines 32 and 30 to fraction collector 29. For parallel operation of the columns 10 and 11, valves 16, 17, 18, 34, 35 and 33 are open and valve 37 is closed, thereby establishing flow through line 13, lines 14 and 15, lines 31 and 32, and line 30 to fraction collector 29. Line 30 is also connected to line 20 via valve 22 which provides a recycle line back to inlet line 19 of metering pump 12. Pumps for use in this invention may be any suitable type of pumps such as, for example, a low pressure peristaltic pump, a diaphragm pump or a gear pump.

Fraction collector 29 is also provided with a plurality of exit ports, taps or fraction outlets (seven in this embodiment) to enable siphoning off one or more sample fractions as they are discharged from columns 10 and/or 11. A pair of line taps 38 and 39 which constitute a stream splitter arrangement, connect line 30 with a detector 40 (to detect a measurable signal or parameter such as uv, visible or infrared absorption or emission, fluorescence, electrochemical potential, conductivity, radioactivity etc). The stream splitter or bypass arrangement may be necessary in a production environment where it may not be feasible to have large flows directed through the detector. In analytical situations, the detector will be on line (i.e., connected directly to line 30). The stream splitter arrangement will need the appropriate valving to ensure that the same linear velocity is maintained in line 30 as in the detector loop. This would ensure that detection of peaks and elution time is not affected by the bypass arrangement. The detector 40 is also operationally connected to a data acquisition system 41 and fraction collector 29 as indicated by broken lines 42 and 43, for reasons described below.

A pressure measuring device 44 and a flow measuring device 45 are connected to line 13 by lines 46 and 47, respectively. Flow measuring device is operationally connected to lines 14 and 15 between valves 17 and 18 and columns 10 and 11, respectively, as indicated by broken lines 48 and 49.

While not shown, the valves 16, 17, 18, 33, 34, 35 and 37 may be connected to a process controller (a mini or micro-processor) or computer system which can be programmed to control the flow through the various valves and thus control the fluid flow through the metering pump 12 and through columns 10 and 11. Flow measuring device 45 which compares and controls the flow through line 13 with that through lines 14 and 15, downstream of valves 17 and 18 can also be connected to the mini or micro-processor to provide a feedback thereto. The data acquisition system 41, may be operationally connected (not shown) to the pressure measuring device 44 and flow measuring device 45, to receive operational signals relative to pressure and flow rate on the input side of the system, as well as to valves 21, 22 and 26–28 for controlling the amount of the sample fluid, recycling fluid and buffers A,B and C flowing into metering pump 12.

As the fluid flows through detector 40, it measures a selected signal or parameter of one or more components as a function of the concentration of the component(s) and as a function of time and/or flow rate and transmit the data to the data acquisition system 41 where it is collected, sorted and stored, as a function of time, flow rate or any other programmed parameter. The fluid flows from and through the detector 40 to the fraction collector 29 where the various fractions are collected for further analysis or for production purposes.

While FIG. 1 illustrates two horizontal flow chromatography columns and associated piping and valves, the invention is not limited to only two columns. Additional columns connected in series, parallel or series-parallel arrangements may be utilized. Each additional column would require appropriate valving, piping etc., necessary to tie the columns into the system shown.

The embodiment of the system illustrated in FIG. 2, utilizes a single horizontal (radial) flow chromatography column for continuous gradient chromatography applications. The basic components of this system are generally similar to those of the system of FIG. 1, the difference being primarily in the manner in which the fluid to be separated is fed into the column. As shown, the system of FIG. 2 includes a horizontal chromatography column 50, which may be of the type described and claimed in the copending applications referred to above, which is connected on the inlet side thereof to a fluid injection mechanism generally indicated at 51 via a fluid line (pipe, tube, conduit) 52, and which in turn is connected on the outlet side thereof to a fraction collector 53 via a line 54 having spaced valves 55 and 56 therein. The injection mechanism 51 includes an injection valve 57 connected to line 52, an injection device 58 (e.g., syringe, or autosampler) positioned in a line 59 connecting a sample source 60 with injector valve 57, and a sample loop line or reservoir mechanism 61 interconnecting lines 52 and 59 (which may be in the form of a coil to control the length thereof), pr a reservoir with appropriate valving for larger sample. While only one column is shown in FIG. 2, the system of this invention may include a plurality of chromatographic column as described earlier.

A mixer 62 is connected to injector valve 57 by a line 63 and via lines 64, 65 and 66 to an outlet side of a pair of pumps 67 and 68. Pump 67 is connected on the inlet side by a line 69 having a valve 70 therein to a source for buffer material A, while pump 68 is connected on the inlet side by a line 71 having a valve 72 therein to a source for buffer material B. A line 73 connects lines 69 and 71 downstream of valves 70 and 72 and is provided with a pair of spaced valves 74 and 75. A recycle line 76 is connected at one end to line 73 intermediate valves 74 and 75 and connected at the opposite end to line 54, a valve 77 being located in recycle line 76.

A detector 78 is connected to line 54 by line taps 79 and 80, with line tap 79 having a valve 81 therein, line tap 79 being located upstream of valve 55. Fraction collector 53 is provided with a plurality of ports or fraction outlets indicated at Fr.1, Fr.2, . . . Fr.8. The detector 78 is connected to a data acquisition system 82 and to fraction collector 53 as indicated by broken lines 83 and 84. The detector 78 may be of the types exemplified above in the embodiment of FIG. 1, and functions to identify, separate or measure the nature and amounts of the various components separated from the sample mixture.

A flow measuring device 85 and a pressure measuring device 86 are connected to line 52 upstream of column 50 via lines 87 and 88, respectively. A process controller/gradient programmer 89 is connected by broken lines 90 and 91 to pumps 67 and 68, and connected to injector valve 57, flow measuring device 85 and pressure measuring device 86 by broken lines 92, 93 and 94. The process controller/gradient programmer 89 functions to control flow rates of sample fluid, buffer materials through the flow measuring device 85, pressure of the pumps, etc.

In operation, the chromatography system of this invention may be used to isolate, for example, certain types of immunoglobulins, such as IgG, from bovine serum in quantity. Columns 10 and 11 may be in packed with DEAE cellulose or cross-linked DEAE agarose or some other similar anion-exchanger. The two columns may be used in parallel if higher throughput is desired. If a higher resolution is desired, the columns may be arranged to be in series relationship. If the sample is not highly purified, the first column may be pre-filled with low exclusion gel filtration material and used as a guard column in series with the second main ion exchange column.

Under operational conditions, the sample reservoir would generally contain the sample in 1:2 or 1:3 dilution with starting buffer which may be 0.05 M Tris-HCl at a pH of about 7.1. The reservoir for Buffer A would contain the starting buffer, 0.05 M Tris-HCl. Buffer B, which is the elution buffer, may contain both 0.05 M Tris-HCl and 0.5 M NaCl at a pH of about 7.1. The high ionic strength buffer is generally used as an eluant buffer. Buffer C may consist of a high strength ionic solution, such as, for example, 1 M NaOH, to wash any unbound species off the packing material at the end of the separation operation.

The isolation of IgG by column chromatography, is traditionally accomplished by loading the sample onto the column in a low ionic strength buffer. The IgG is essentially not bound to the packing material and the other components such as albumin, transferrin and the like are bound. Once the IgG is eluted from the column, a high ionic strength buffer is used to remove the other bound proteins or other species. Final clean up may be performed by using an even higher ionic strength buffer such as 1 M NaOH. Thereafter, the column is recalibrated with the starting buffer and is ready for the next cycle.

At the start of the initial run, valves 21, 17, 18, 33, 34 and 35 are open, and valves 23, 24, 25 and 37 are closed. The sample is applied by turning on pump 12 and pumping in a measured volume of the sample onto the packed columns 10 and 11. This may be accomplished via a totalising or timing system which may be part of the pump assembly or attached to the flow measuring device. For this exemplary separation, if the total volume of the column is about 400 ml, about 1 gm of protein may be loaded in about 100 ml diluted volume. The sample may be pumped in at the regular operating flow rate of about 75–100 ml/min.

After the sample is loaded, valve 21 is closed and valve 26 is opened. The starting buffer which is the low ionic strength buffer is used to elute any unbound protein fractions from the column. The eluted components may be passed directly through a detector placed in line 30 or if a large enough cell is not available, it may be used with a stream splitter as shown in FIG. 1. Both tubings 38 and 39 should be selected to have the same size so that the pressure drop in the side stream is the same as in line 30. This may be achieved by the use of a pinch clamp or a metering valve provided on line 30. The detector measures the absorbance (uv at 254 or 280 nm) of the IgG peak. An output signal (voltage, current, or frequency based) is sent to the data acquisition system where it is stored and recorded simultaneously. Other operating parameters such as flow rate, injection time and the like may also be programmed to be stored and recorded. The recording is generally in terms of an outline plot of the absorbance as a function of flow rate or time. A graph of the pressure drop as a function of flow rate is presented in FIG. 4. The plot shows that using the columns of the present invention, the back pressure and bed compression are minimal for flow rates between about 80 ml/min to about 120 ml/min.

The detector may also be arranged to interface with the fraction collector. The fraction collector may be programmed to collect fractions of the eluant stream on either a manual mode or a time based mode or peak collection mode. In this example, the peak detection mode was used because it was intended to collect the entire IgG peak. The peak collection mechanism is activated if the signal from the detector exceeds a preset threshold level. When the signal drops below the threshold level, the peak collection stops and the effluent or eluant is collected at the next stage or at the fraction collector.

When the IgG peak has eluted, valve 27 may be closed and valve 28 opened in order to pump high ionic strength buffer C through the column to elute the remaining compounds bound to the column components. These remainder components may be eluted as closely eluting species and may be collected in the fraction collector as one or several fractions, depending on the use for these compounds. If greater resolution of separation between any of these species is desired, the fraction collector is turned off, valve 28 closed and valve 22 opened, and the eluant recycled through the column until the desired level of separation is achieved. The separated components may then be collected in the fraction collector.

In FIG. 2, the essential structure of the system and its operation is essentially the same as that of the embodiment illustrated in FIG. 1, except for the solvent delivery components. In the embodiment of FIG. 1, solvent conditions could only be changed in a stepwise mode because of the use of on/off valves and a single pump. In the embodiment of FIG. 2, two pumps are used along with a mixer and gradient programmer to allow the user to generate continuous gradients of ionic strength or pH to achieve superior separation between closely eluting or unresolved components, such as between transferrin and albumin in the example described herein.

The required gradient to vary ionic strength or pH, (for example, to vary ionic strength from 0 to 0.5 M NaCl in one step rather than by physically switching buffers at desired time intervals), may be programmed into the gradient programmer to create concave or convex gradients, which then controls the pump flow rates. For example, at the start of the gradient, pump 67 may be operating at about 100 ml/min and pump 68 may not be in operation. After a preset time interval, pump 67 may be slowed to about 98 ml/min and pump 68 may be operated at about 2 ml/min. Thus, even though the total flow rate has not changed, the composition has been altered and the ionic strength increased. Gradually, pump 68 delivers a greater flow and pump 67 correspondingly, a lower flow, until at the end of the gradient, pump 67 is stopped and pump 68 operates at about 100 ml/min. This may also be achieved by the use of two control valves and one pump.

The mixer 62 in line 63 functions to mix the fluids from pumps 67 and 68. The injector which may be in the form of a pump, syringe and sample loop, autosampler, or gravity fed reservoir, is now placed downstream of the mixer to avoid mixing of buffer with the sample and to increase its proximity to the columns.

In the separation of IgG described herein, a linear gradient from 0 to 0.5 M NaCl was used to perform the same separation and the gradient was spanned over a period of about 45 minutes. 1.25 gms of protein was loaded onto the column and base line resolution of all components was achieved within one hour at a flow rate of 85 ml/min. The peak separation of each of the compounds was now pronounced and a better base line separation was achieved as shown in FIG. 5. In FIG. 5, the first peak represents IgG, the second peak is transferrin and the third peak is albumin with other serum proteins. The operating conditions for the separation illustrated in FIG. 5, were as follows:

Sample: Bovine Serum—1.25 gms total protein 17.5 ml diluted 5×
Buffer A: Tris HCl
Buffer B: Tris HCl—0.5 M NaCl
Linear Gradient: 0.05 M NaCl in Tris Buffer
Pressure: 20 psi
Flow Rate: 85 ml/min
Column Packing: DEAE Cellulose
Protein Content: 7.1 gm/100 ml undiluted serum For a scale up of the fractionation of bovine serum described above, the preceding experiment was repeated with twice the protein load. Rapid separation of the individual components was still achieved as shown in FIG. 6.

Sample: 35.0 ml diluted 3×
Flow Rate: 85 ml/min
Buffer: 0.05 M Tris-HCl, pH 7.1
Gradient: 0.5 M NaCl in Tris Buffer
Protein Content: 7.1 gm/100 ml undiluted serum.

FIG. 3 illustrates an embodiment of a stand or support mechanism for the horizontal (radial) chromatography columns of the systems of FIGS. 1 and 2, which enable stacking or ready relocation or movement (such as raise, lower etc.,) of the columns. As shown in FIG. 3, the stand or support mechanism comprises a pair of threaded uprights or rods 100 and 101 secured at lower ends to a bottom plate 102 via threaded apertures 103 (only one shown) and locking nuts 104, and at the upper ends to a top plate 105 via threaded apertures (not shown) and a set of locking nuts 106 and 107 for each rod 100 and 101. The threaded arrangement of top plate 105 allows for height adjustment thereof. For example, the uprights or rods 100 and 101 may have a height of about 2 ft to about 8 ft and a diameter of about ½ inch to about 2 inches and may be constructed of aluminum, steel, iron, galvanized zinc, glass, ceramic, plexiglass, acrylic and the like. The bottom plate 102 may, for example, be constructed of stainless steel, aluminum, galvanized zinc and the like, and has a thickness of about ½ inch to about 3 inches and may be circular with a diameter of about 10 inches to about 40 inches or may be square or rectangular or any other suitable shape and size, with appropriate dimensions to support the rods 100 and 101 so as to prevent tipping of a column retained therein.

The stand includes upper and lower column retainer plates 108 and 109 each having a pair of threaded apertures 110 and 111, respectively, through which rods 100 and 101 extend. A chromatography column 112 is positioned and retained between retainer plates 108 and 109 by lock nuts 113 and 114 respectively on threaded rods 100 and 101. Each of the retainer plates 108 and 109 is provided with a central opening or hole 115 and 116 and a pair of counter sunk grooves 117 and 118. The openings 115 and 116 provide access to fittings and attachments on the column 112 described below, while the grooves 117 and 118 accommodate the ends of (protruding) retainer members, rods or bolts and nuts generally indicated at 119 of column 112. While only two bolts 119 are shown, the column 112 may contain 6,8 or more such retaining bolts in spaced relation thereabout.

The column 112, as shown, is of the type described and claimed in the above-identified application Ser. No. 06/869,295, filed June 2, 1986 (U.S. Patent No. 4,676,898), entitled "Improved Chromatography Column Using Horizontal Flow", which includes a centrally located sample fluid inlet threaded fitting 120 connected to a fluid distributor within the column 112, a separation medium inlet threaded fitting 121 for injecting medium into the column for forming a separation bed therein, an air discharge threaded fitting 122 through which air is removed from the column bed packing to minimize dead volume within the column, and a component or fraction outlet threaded fitting 123 connected to the collection channel within the column. Fittings 120, 121 and 122 extend through opening 115 in upper retainer plate 108, while fitting 123 extends through opening 116 in lower retainer plate 109. Threaded fittings 120–123 are constructed to receive a connector or coupling of associated tubings or lines (not shown).

Retainer plates 108 and 109, in this embodiment are of a circular configuration with grooves 117 and 118 being annular to cooperate with the configuration of the housing of column 112. The retainer plates may, for example, be fabricated or constructed of a metal such as stainless steel or aluminum, or of a plastic or acrylic or similar material, with a diameter of about 10 inches to about 40 inches, and thickness of about ½ inch to about 2 inches. However, other retainer plate configurations may also be utilized.

The stand of FIG. 3 functions as a sturdy support or holder for the column 112 and by movement of the retainer plates 108 and 109 along the length of rods 100 and 101, the column 112 can be raised or lowered, while having ready access to the column fittings 120–123. The stand also serves to prevent the column 112 from damage due to toppling or rolling over. In addition, the stand can be utilized to support a plurality of stacked columns by the addition of sets or retainer plates, such as 108 and 109.

It has thus been shown that the systems and support stand of the present invention provides an advance in the art wherein rapid fluid sample separations can be accomplished at low operating pressures using horizontal (radial) flow chromatography columns. The invention thereby overcomes the problems associated with high pressure chromatography systems and the associated high costs and hazards. The system of this invention is readily adapted for either isocratic, gradient or ternary chromatography separation techniques, as well as for single, multistep, or continuous gradient chromatography.

The foregoing description of the preferred embodiments of the subject invention have been presented for purposes of illustration and description and for a better understanding of the invention. While particular embodiments of the systems and associated column support stand have been illustrated and described, it is not intended to be exhaustive or to limit the invention to the precise form disclosed; and obviously, many modifications and variations as are suited to the particular use contemplated are possible in light of the above teaching and become apparent to those skilled in the art. It is intended that the invention with all such modifications and variations which fall within the scope thereof be defined by the claims appended hereto.

What is claimed is:

1. A low pressure chromatography system using at least one horizontal column, said system comprising:
   at least one chromatographic column having a bed of separation medium located intermediate an inlet channel and an outlet channel said inlet and outlet channels being coaxially positioned with respect to each other, said column being constructed such that sample fluid passes through said bed in a horizontal direction from said inlet channel to said outlet channel,
   means for directing sample fluid to said column including pump means having an outlet connected via a first fluid line to an inlet of said column, said inlet being in fluid communication with said inlet channel, and valve means mounted in said first fluid line for controlling passage of fluid therethrough,
   detection means connected to said column for detecting sample fluid fractions discharged from said outlet channel of said column, and
   means for controlling at least sample fluid directed into said inlet of said column and sample fluid fractions discharged from said outlet channel of said column.

2. The system of claim 1, additionally including fraction collector means connected to said detector means for collection of fractions of sample fluid discharged from said outlet of said column.

3. The system of claim 2, additionally including a second chromatography column constructed as said first-mentioned column, inlet fluid lines connecting said sample fluid directing means to each of said columns, outlet fluid lines connecting each of said columns to said detection means and/or said fraction collector means, an interconnecting fluid line connected at one end to said inlet fluid lines intermediate said columns and at an opposite end to said outlet fluid lines intermediate said columns, and valve means located in said inlet fluid lines, said outlet fluid lines and said interconnecting fluid line, such that sample fluid can be directed into said columns in series or in parallel relation.

4. The system of claim 1 or 2, additionally including means for measuring pressure and means for measuring flow of sample fluid into said inlet of said column, each of said means being operatively connected to said system intermediate said pump means and said column.

5. The system of claim 4, additionally including a data acquisition system operatively connected to at least said detector.

6. The system of claim 5, additionally including a process controller/gradient programmer operatively connected to at least said sample fluid directing means.

7. The system of claim 6, wherein said process controller/gradient programmer is additionally operatively connected to said means for measuring flow and pressure of sample fluid directed into said column.

8. The system of claim 1 or 2, wherein said pump means has an inlet adapted to be connected to at least a sample fluid source.

9. The system of claim 8, wherein said inlet of said pump means is connected to said sample fluid source and to at least one buffer material source, and additionally including valves for controlling flow of sample fluid and buffer material.

10. The system of claim 8, wherein said inlet of said pump means is connected to a second fluid line, said second fluid line is connected to said source of sample fluid, said second fluid line being also connected to a plurality of fluid lines connected to a plurality of different buffer material sources, a valve means connected so as to control flow of sample material into second said fluid line, and a plurality of individual valve means connected in said plurality of fluid lines so as to control flow of the different buffer materials in said second fluid line.

11. The system of claim 9, additionally including another fluid line interconnecting said fraction collector means with said second fluid line, and valve means connected to said another fluid line so as to control flow of fluid from said fraction collector means to said pump means.

12. The system of claim 1 or 2, wherein said column is additionally provided with
means by which separation medium may be directed thereinto to form said bed, and
means by which air may be discharged therefrom for preventing void volume therein.

13. The system of claim 1 or 2, wherein said sample fluid directing means includes:
a valve located in a first fluid line positioned intermediate said column and a fluid mixer,
an injector means for directing a sample fluid to said valve,
a plurality of pumps connected to said fluid mixer, and
means for directing buffer material to said plurality of pumps.

14. The system of claim 13, additionally including a second fluid line having one end connected to said first fluid line intermediate said column and said valve, with an opposite end connected intermediate said valve and said injector means, said injector means being adapted to be connected to a source of sample fluid.

15. The system of claim 13, wherein said plurality of pumps is connected to an inlet of said fluid mixer in parallel relation, and wherein said means for directing buffer material to said plurality of pumps comprises:
a pair of fluid lines each connected at one end to an inlet of an associated pump with an opposite end adapted to be connected to a source of buffer material, an interconnecting fluid line connecting said pair of lines,
a valve located in each of said pair of fluid lines upstream of said interconnecting fluid line and
at least one valve located in said interconnecting fluid line.

16. The system of claim 15, wherein said interconnecting fluid line is provided with a pair of spaced apart valves, and additionally including a recycle fluid line having one end interconnecting said detector means and said fraction collector means with an opposite end connected to said interconnecting fluid line intermediate said pair of spaced valves, and a valve located in said recycle fluid line.

17. The system of claim 13, additionally including a process controller/gradient programmer operationally connected to said valve and to said plurality of pumps.

18. The system of claim 17, additionally including a flow measuring device and a pressure measuring device, each connected to said first fluid line intermediate said valve and said column, and wherein said process controller/gradient programmer is operationally connected to each of said flow and pressure measuring devices.

19. The system of claim 17, additionally including a data acquisition system operatively connected to at least said detector.

20. The system of claim 1 or 2, additionally including a support mechanism for said chromatography column, said support mechanism comprising:
a bottom plate,
a top plate,
a pair of upright support members located intermediate and secured to said bottom plate and said top plate, and
a pair of retainer plates positioned intermediate said bottom plate and said top plate and adjustably mounted to said pair of support members,
said column being positioned between and retained by said pair of retainer plates.

21. The system of claim 20, wherein said pair of retainer plates each includes an opening therein and a groove spaced from said opening, said opening being constructed to allow fittings on said column to extend through said retainer plates, said grooves being constructed to receive protruding retainer members of said column.

22. The system of claim 20, wherein said pair of support members are provided with threads along at least sections thereof, and additionally including a plurality of locking nuts on said threaded sections of said support members, said locking nuts functioning to retain at least said pair of retainer plates in fixed relation to said support members wherein said column is positioned between said retainer plates.

* * * * *